US009224311B2

(12) United States Patent
Yeh et al.

(10) Patent No.: US 9,224,311 B2
(45) Date of Patent: *Dec. 29, 2015

(54) COMBINING DATA SOURCES TO PROVIDE ACCURATE EFFORT MONITORING

(71) Applicant: SONY CORPORATION, Tokyo (JP)

(72) Inventors: Sabrina Tai-Chen Yeh, Laguna Beach, CA (US); Jenny Therese Fredriksson, San Diego, CA (US)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,663

(22) Filed: Apr. 17, 2014

(65) Prior Publication Data

US 2015/0081056 A1    Mar. 19, 2015

Related U.S. Application Data

(63) Continuation of application No. 14/037,224, filed on Sep. 25, 2013, now Pat. No. 8,795,138.

(60) Provisional application No. 61/878,835, filed on Sep. 17, 2013.

(51) Int. Cl.
| | |
|---|---|
| A63B 71/00 | (2006.01) |
| G09B 19/00 | (2006.01) |
| G01S 19/19 | (2010.01) |
| G06F 19/00 | (2011.01) |
| G06Q 10/06 | (2012.01) |
| A61B 5/0205 | (2006.01) |
| A61B 5/021 | (2006.01) |
| A61B 5/024 | (2006.01) |
| A61B 5/00 | (2006.01) |
| A63B 71/06 | (2006.01) |

(Continued)

(52) U.S. Cl.
CPC ............ *G09B 19/0038* (2013.01); *A61B 5/021* (2013.01); *A61B 5/02055* (2013.01); *A61B 5/02438* (2013.01); *A61B 5/4815* (2013.01); *A63B 71/06* (2013.01); *G01C 21/00* (2013.01); *G01C 21/20* (2013.01); *G01S 19/19* (2013.01);
(Continued)

(58) Field of Classification Search
CPC ...... A63B 24/00; A63B 71/06; G09B 19/0038
USPC ......................................... 482/1–9, 900–902
See application file for complete search history.

(56) References Cited

U.S. PATENT DOCUMENTS

| | | |
|---|---|---|
| 4,278,095 A | 7/1981 | Lapeyre |
| 4,566,461 A | 1/1986 | Lubell et al. |

(Continued)

FOREIGN PATENT DOCUMENTS

| | | |
|---|---|---|
| JP | H08241496 A | 9/1996 |
| JP | H10281790 A | 10/1998 |

(Continued)

OTHER PUBLICATIONS

Judith A. Markowitz, "Voice Biometrics, Who Are You? Your voice along can be used to verify your personal identity—unobtrusively and invisibly." Sep. 2000/ vol. 43. No. 9, Communications of the ACM. http://www.web2.utc.edu/~djy471/documents/voice-biometrics-p66-markowitz.pdf.

(Continued)

*Primary Examiner* — Glenn Richman
(74) *Attorney, Agent, or Firm* — John L. Rogitz

(57) ABSTRACT

By combining data from different sensors (on fitness device, mobile smartphone, smart clothing, other devices or people in same location), an intelligent system provides a better indicator of an individual's physical effort, using rich data sources to enhance quantified metrics such as distance/pace/altitude gain, to provide a clearer picture of an individual's exercise and activity.

20 Claims, 4 Drawing Sheets

(51) Int. Cl.

| | | |
|---|---|---|
| *G06F 17/30* | (2006.01) | |
| *G06F 3/16* | (2006.01) | |
| *H04B 5/00* | (2006.01) | |
| *G01C 21/20* | (2006.01) | |
| *G06F 3/01* | (2006.01) | |
| *G08B 25/01* | (2006.01) | |
| *G10L 15/00* | (2013.01) | |
| *G01C 21/00* | (2006.01) | |
| *G06F 3/0481* | (2013.01) | |
| *G06F 3/0484* | (2013.01) | |
| *H04L 29/06* | (2006.01) | |
| *H04W 4/00* | (2009.01) | |
| *H04W 12/08* | (2009.01) | |
| *A61B 5/11* | (2006.01) | |
| *H04M 1/725* | (2006.01) | |
| *A61B 5/117* | (2006.01) | |
| *A61B 5/145* | (2006.01) | |

(52) U.S. Cl.
CPC .............. *G06F 3/017* (2013.01); *G06F 3/0481* (2013.01); *G06F 3/0484* (2013.01); *G06F 3/165* (2013.01); *G06F 17/3074* (2013.01); *G06F 19/3481* (2013.01); *G06Q 10/0639* (2013.01); *G08B 25/016* (2013.01); *G10L 15/00* (2013.01); *H04B 5/0025* (2013.01); *H04L 63/0853* (2013.01); *H04W 4/008* (2013.01); *H04W 12/08* (2013.01); *A61B 5/11* (2013.01); *A61B 5/1172* (2013.01); *A61B 5/1176* (2013.01); *A61B 5/14532* (2013.01); *A61B 5/14542* (2013.01); *H04M 1/7253* (2013.01); *H04M 2250/02* (2013.01); *H04M 2250/04* (2013.01); *H04M 2250/12* (2013.01)

(56) References Cited

U.S. PATENT DOCUMENTS

| | | |
|---|---|---|
| 4,625,962 A | 12/1986 | Street |
| 4,708,337 A | 11/1987 | Shyu |
| 4,728,100 A | 3/1988 | Smith |
| 4,869,497 A | 9/1989 | Stewart et al. |
| 4,916,628 A | 4/1990 | Kugler |
| 4,920,969 A | 5/1990 | Suzuki et al. |
| 5,072,458 A | 12/1991 | Suzuki |
| 5,111,818 A | 5/1992 | Suzuki et al. |
| 5,207,621 A | 5/1993 | Koch et al. |
| 5,277,197 A | 1/1994 | Church et al. |
| 5,314,389 A | 5/1994 | Dotan |
| 5,410,472 A | 4/1995 | Anderson |
| 5,433,683 A | 7/1995 | Stevens |
| 5,454,770 A | 10/1995 | Stevens |
| 5,474,083 A | 12/1995 | Church et al. |
| 5,474,090 A | 12/1995 | Begun et al. |
| 5,516,334 A | 5/1996 | Easton |
| 5,524,637 A | 6/1996 | Erickson |
| 5,579,777 A | 12/1996 | Suga |
| 5,598,849 A | 2/1997 | Browne |
| 5,704,067 A | 1/1998 | Brady |
| 5,706,822 A | 1/1998 | Khavari |
| 5,857,939 A | 1/1999 | Kaufman |
| 5,921,891 A | 7/1999 | Brown |
| 6,013,007 A | 1/2000 | Root et al. |
| 6,032,108 A | 2/2000 | Seiple et al. |
| 6,042,519 A | 3/2000 | Shea |
| 6,050,924 A | 4/2000 | Shea |
| 6,101,443 A | 8/2000 | Kato et al. |
| 6,106,297 A | 8/2000 | Pollak et al. |
| 6,171,218 B1 | 1/2001 | Shea |
| 6,198,431 B1 | 3/2001 | Gibson |
| 6,220,865 B1 | 4/2001 | Macri et al. |
| 6,231,527 B1 | 5/2001 | Sol |
| 6,244,988 B1 | 6/2001 | Delman |
| 6,251,048 B1 | 6/2001 | Kaufman |
| 6,259,944 B1 | 7/2001 | Margulis et al. |
| 6,296,595 B1 | 10/2001 | Stark et al. |
| 6,447,425 B1 | 9/2002 | Keller et al. |
| 6,464,618 B1 | 10/2002 | Shea |
| 6,497,638 B1 | 12/2002 | Shea |
| 6,500,100 B1 | 12/2002 | Harrell |
| 6,515,593 B1 | 2/2003 | Stark et al. |
| 6,582,342 B2 | 6/2003 | Kaufman |
| 6,601,016 B1 | 7/2003 | Brown et al. |
| 6,605,044 B2 | 8/2003 | Bimbaum |
| 6,638,198 B1 | 10/2003 | Shea |
| 6,659,916 B1 | 12/2003 | Shea |
| 6,659,946 B1 | 12/2003 | Batchelor et al. |
| 6,672,991 B2 | 1/2004 | O'Malley |
| 6,702,719 B1 | 3/2004 | Brown et al. |
| 6,746,371 B1 | 6/2004 | Brown et al. |
| 6,749,537 B1 | 6/2004 | Hickman |
| 6,786,848 B2 | 9/2004 | Yamashita et al. |
| 6,793,607 B2 | 9/2004 | Neil |
| 6,863,641 B1 | 3/2005 | Brown et al. |
| 6,866,613 B1 | 3/2005 | Brown et al. |
| 6,882,883 B2 | 4/2005 | Condie et al. |
| 6,997,882 B1 | 2/2006 | Parker et al. |
| 7,024,369 B1 | 4/2006 | Brown et al. |
| 7,056,265 B1 | 6/2006 | Shea |
| 7,057,551 B1 | 6/2006 | Vogt |
| 7,070,539 B2 | 7/2006 | Brown et al. |
| 7,128,693 B2 | 10/2006 | Brown et al. |
| 7,192,401 B2 | 3/2007 | Salaasti et al. |
| 7,223,215 B2 | 5/2007 | Bastyr |
| 7,227,468 B1 | 6/2007 | Florio |
| 7,245,254 B1 | 7/2007 | Vogt |
| 7,328,612 B2 | 2/2008 | Jämsen et al. |
| 7,351,187 B2 | 4/2008 | Seliber |
| 7,370,763 B1 | 5/2008 | Pascucci |
| 7,376,423 B2 | 5/2008 | Sakanaba |
| 7,438,670 B2 | 10/2008 | Gray et al. |
| 7,507,183 B2 | 3/2009 | Anderson et al. |
| 7,586,418 B2 | 9/2009 | Cuddihy et al. |
| 7,617,615 B1 | 11/2009 | Martorell et al. |
| 7,633,076 B2 | 12/2009 | Huppi et al. |
| 7,664,292 B2 | 2/2010 | Van Den et al. |
| 7,683,252 B2 | 3/2010 | Oliver et al. |
| 7,699,752 B1 | 4/2010 | Anderson et al. |
| 7,728,214 B2 | 6/2010 | Oliver et al. |
| 7,786,856 B2 | 8/2010 | O'Brien |
| 7,840,031 B2 | 11/2010 | Albertson et al. |
| 7,841,966 B2 | 11/2010 | Aaron et al. |
| 7,857,730 B2 | 12/2010 | Dugan |
| 7,894,849 B2 | 2/2011 | Kass et al. |
| 7,931,563 B2 | 4/2011 | Shaw et al. |
| 7,951,046 B1 | 5/2011 | Barber, Jr. |
| 7,966,230 B2 | 6/2011 | Brown |
| 7,979,136 B2 | 7/2011 | Young et al. |
| 7,996,080 B1 | 8/2011 | Hartman et al. |
| 8,021,270 B2 | 9/2011 | D'eredita |
| 8,029,410 B2 | 10/2011 | Shea |
| 8,047,965 B2 | 11/2011 | Shea |
| 8,057,360 B2 | 11/2011 | Shea |
| 8,062,182 B2 | 11/2011 | Somers |
| 8,092,346 B2 | 1/2012 | Shea |
| 8,103,762 B2 | 1/2012 | Duberry |
| 8,109,858 B2 | 2/2012 | Redmann |
| 8,125,314 B2 | 2/2012 | Fithian et al. |
| 8,157,730 B2 | 4/2012 | LaBoeuf et al. |
| 8,162,802 B2 | 4/2012 | Berg |
| 8,182,424 B2 | 5/2012 | Heckerman |
| 8,199,014 B1 | 6/2012 | Kindeberg |
| 8,204,786 B2 | 6/2012 | LaBoeuf et al. |
| 8,219,191 B1 | 7/2012 | Hartman et al. |
| 8,277,377 B2 | 10/2012 | Quy |
| 8,317,658 B2 | 11/2012 | Dorogusker et al. |
| 8,333,874 B2 | 12/2012 | Currie |
| 8,343,012 B2 | 1/2013 | Redmann |
| 8,360,785 B2 | 1/2013 | Park et al. |
| 8,360,935 B2 | 1/2013 | Olsen et al. |
| 8,371,990 B2 | 2/2013 | Shea |
| 8,406,085 B2 | 3/2013 | Sakita |

(56) References Cited

U.S. PATENT DOCUMENTS

| | | |
|---|---|---|
| 8,435,177 B2 | 5/2013 | Lanfermann et al. |
| 8,452,413 B2 | 5/2013 | Young et al. |
| 8,467,860 B2 | 6/2013 | Salazar et al. |
| 8,491,446 B2 | 7/2013 | Hinds et al. |
| 8,512,209 B2 | 8/2013 | Guidi et al. |
| 8,512,548 B2 | 8/2013 | Bar-or et al. |
| 8,514,067 B2 | 8/2013 | Hyde et al. |
| 8,597,093 B2 | 12/2013 | Engelberg et al. |
| 8,795,138 B1 | 8/2014 | Yeh et al. |
| 8,825,445 B2 | 9/2014 | Hoffman et al. |
| 2001/0020143 A1 | 9/2001 | Stark et al. |
| 2002/0028730 A1 | 3/2002 | Kaufman |
| 2002/0072932 A1 | 6/2002 | Swamy |
| 2002/0082142 A1 | 6/2002 | Cannon et al. |
| 2002/0108000 A1 | 8/2002 | Iori et al. |
| 2002/0128119 A1 | 9/2002 | Arai |
| 2002/0142887 A1 | 10/2002 | O'Malley |
| 2002/0156392 A1 | 10/2002 | Arai et al. |
| 2003/0028116 A1 | 2/2003 | Birnbaum |
| 2003/0064860 A1 | 4/2003 | Yamashita et al. |
| 2003/0171188 A1 | 9/2003 | Neil |
| 2003/0171189 A1 | 9/2003 | Kaufman |
| 2003/0211916 A1 | 11/2003 | Capuano |
| 2003/0226695 A1 | 12/2003 | Mault |
| 2004/0058908 A1 | 3/2004 | Keller et al. |
| 2004/0077462 A1 | 4/2004 | Brown et al. |
| 2004/0117214 A1 | 6/2004 | Shea |
| 2005/0010426 A1 | 1/2005 | Chen et al. |
| 2005/0070809 A1 | 3/2005 | Acres |
| 2005/0075214 A1 | 4/2005 | Brown et al. |
| 2005/0083846 A1 | 4/2005 | Bahl |
| 2005/0163346 A1 | 7/2005 | Van Den et al. |
| 2005/0177059 A1 | 8/2005 | Koivumaa et al. |
| 2005/0209002 A1 | 9/2005 | Blythe et al. |
| 2005/0233861 A1 | 10/2005 | Hickman et al. |
| 2005/0272561 A1 | 12/2005 | Cammerata |
| 2006/0020216 A1 | 1/2006 | Oishi et al. |
| 2006/0025282 A1 | 2/2006 | Redmanm |
| 2006/0032315 A1 | 2/2006 | Saalastic et al. |
| 2006/0058156 A1 | 3/2006 | Cohen et al. |
| 2006/0094570 A1 | 5/2006 | Schneider |
| 2006/0107822 A1 | 5/2006 | Bowen |
| 2006/0111944 A1 | 5/2006 | Sirmans, Jr. et al. |
| 2006/0113381 A1 | 6/2006 | Hochstein et al. |
| 2006/0240959 A1 | 10/2006 | Huang |
| 2006/0252602 A1 | 11/2006 | Brown et al. |
| 2006/0281976 A1 | 12/2006 | Juang et al. |
| 2006/0288846 A1 | 12/2006 | Logan |
| 2007/0033068 A1 | 2/2007 | Rao et al. |
| 2007/0033069 A1 | 2/2007 | Rao et al. |
| 2007/0042868 A1 | 2/2007 | Fisher et al. |
| 2007/0060446 A1 | 3/2007 | Asukai et al. |
| 2007/0083092 A1 | 4/2007 | Rippo et al. |
| 2007/0083095 A1 | 4/2007 | Rippo et al. |
| 2007/0113725 A1 | 5/2007 | Oliver et al. |
| 2007/0113726 A1 | 5/2007 | Oliver et al. |
| 2007/0146116 A1 | 6/2007 | Kimbrell |
| 2007/0173377 A1 | 7/2007 | Jamsen et al. |
| 2007/0213608 A1 | 9/2007 | Brown |
| 2007/0219059 A1 | 9/2007 | Schwartz et al. |
| 2007/0249467 A1 | 10/2007 | Hong et al. |
| 2007/0249468 A1 | 10/2007 | Chen |
| 2007/0266065 A1 | 11/2007 | Rosenberg |
| 2007/0275825 A1 | 11/2007 | O'Brien |
| 2007/0300185 A1 | 12/2007 | Macbeth et al. |
| 2008/0045384 A1 | 2/2008 | Matsubara et al. |
| 2008/0051919 A1 | 2/2008 | Sakai et al. |
| 2008/0098876 A1 | 5/2008 | Kuo et al. |
| 2008/0103022 A1 | 5/2008 | Dvorak et al. |
| 2008/0110115 A1 | 5/2008 | French |
| 2008/0146890 A1 | 6/2008 | LaBoeuf et al. |
| 2008/0146892 A1 | 6/2008 | LaBoeuf et al. |
| 2008/0147502 A1 | 6/2008 | Baker |
| 2008/0153670 A1 | 6/2008 | McKirdy et al. |
| 2008/0162186 A1 | 7/2008 | Jones |
| 2008/0170123 A1 | 7/2008 | Albertson et al. |
| 2008/0176713 A1 | 7/2008 | Olivera et al. |
| 2008/0182723 A1 | 7/2008 | Aaron et al. |
| 2008/0204225 A1 | 8/2008 | Kitchen |
| 2008/0220941 A1 | 9/2008 | Shaw et al. |
| 2008/0262918 A1 | 10/2008 | Wiener |
| 2009/0044687 A1 | 2/2009 | Sorber |
| 2009/0105047 A1 | 4/2009 | Guidi et al. |
| 2009/0131224 A1 | 5/2009 | Yuen |
| 2009/0131759 A1 | 5/2009 | Sims et al. |
| 2009/0138488 A1 | 5/2009 | Shea |
| 2009/0149131 A1 | 6/2009 | Young et al. |
| 2009/0150175 A1 | 6/2009 | Young et al. |
| 2009/0233771 A1 | 9/2009 | Quatrochi et al. |
| 2009/0247366 A1 | 10/2009 | Frumer |
| 2009/0247368 A1 | 10/2009 | Chiang |
| 2009/0258758 A1 | 10/2009 | Hickman et al. |
| 2009/0275442 A1 | 11/2009 | Nissila |
| 2009/0287103 A1 | 11/2009 | Pillai |
| 2009/0292178 A1 | 11/2009 | Ellis et al. |
| 2009/0293298 A1 | 12/2009 | Martorell et al. |
| 2009/0298426 A1 | 12/2009 | Helvick |
| 2010/0017114 A1 | 1/2010 | Tehan et al. |
| 2010/0035726 A1 | 2/2010 | Fisher et al. |
| 2010/0056341 A1* | 3/2010 | Ellis et al. .......................... 482/9 |
| 2010/0120585 A1 | 5/2010 | Quy |
| 2010/0134257 A1 | 6/2010 | Puleston et al. |
| 2010/0167876 A1 | 7/2010 | Cheng |
| 2010/0185062 A1 | 7/2010 | Salazar et al. |
| 2010/0186078 A1 | 7/2010 | Napoli et al. |
| 2010/0190607 A1 | 7/2010 | Widerman et al. |
| 2010/0216603 A1 | 8/2010 | Somers |
| 2010/0217099 A1 | 8/2010 | LaBoeuf et al. |
| 2010/0222178 A1 | 9/2010 | Shea |
| 2010/0222181 A1 | 9/2010 | Shea |
| 2010/0234699 A1 | 9/2010 | Lanfermann et al. |
| 2010/0273610 A1 | 10/2010 | Johnson |
| 2011/0001827 A1 | 1/2011 | Ortiz et al. |
| 2011/0015039 A1 | 1/2011 | Shea |
| 2011/0015041 A1 | 1/2011 | Shea |
| 2011/0035184 A1 | 2/2011 | Aaron et al. |
| 2011/0059825 A1 | 3/2011 | McGown |
| 2011/0098112 A1 | 4/2011 | LaBoeuf et al. |
| 2011/0098583 A1 | 4/2011 | Pandia et al. |
| 2011/0106627 A1 | 5/2011 | Laboeuf et al. |
| 2011/0137191 A1 | 6/2011 | Kinnunen |
| 2011/0165996 A1 | 7/2011 | Paulus et al. |
| 2011/0165998 A1 | 7/2011 | Lav et al. |
| 2011/0179068 A1 | 7/2011 | O'Brien |
| 2011/0195780 A1 | 8/2011 | Lu |
| 2011/0195819 A1 | 8/2011 | Shaw et al. |
| 2011/0205697 A1 | 8/2011 | Callicoat et al. |
| 2011/0212688 A1 | 9/2011 | Griffin et al. |
| 2011/0230142 A1 | 9/2011 | Young et al. |
| 2011/0246908 A1 | 10/2011 | Akram et al. |
| 2011/0263385 A1 | 10/2011 | Shea et al. |
| 2011/0275042 A1 | 11/2011 | Warman et al. |
| 2011/0288381 A1 | 11/2011 | Bartholomew et al. |
| 2011/0319228 A1 | 12/2011 | Shea |
| 2012/0010478 A1 | 1/2012 | Kinnunen et al. |
| 2012/0058859 A1 | 3/2012 | Elsom-Cook et al. |
| 2012/0077580 A1 | 3/2012 | Mahajan et al. |
| 2012/0108395 A1 | 5/2012 | Shea |
| 2012/0129138 A1 | 5/2012 | Redmann |
| 2012/0130630 A1 | 5/2012 | Tang et al. |
| 2012/0142429 A1 | 6/2012 | Muller |
| 2012/0178431 A1 | 7/2012 | Gold |
| 2012/0184871 A1 | 7/2012 | Jang et al. |
| 2012/0190502 A1 | 7/2012 | Paulus et al. |
| 2012/0203081 A1 | 8/2012 | LaBoeuf et al. |
| 2012/0226111 A1 | 9/2012 | LaBoeuf et al. |
| 2012/0226112 A1 | 9/2012 | LaBoeuf et al. |
| 2012/0271913 A1 | 10/2012 | Tallgren et al. |
| 2012/0283855 A1 | 11/2012 | Hoffman et al. |
| 2012/0308192 A1 | 12/2012 | Chung et al. |
| 2013/0032634 A1 | 2/2013 | McKirdy |
| 2013/0046477 A1 | 2/2013 | Hyde et al. |
| 2013/0089842 A1 | 4/2013 | Shea |
| 2013/0090213 A1 | 4/2013 | Amini et al. |

(56) References Cited

U.S. PATENT DOCUMENTS

| | | | |
|---|---|---|---|
| 2013/0090565 A1 | 4/2013 | Quy | |
| 2013/0095459 A1 | 4/2013 | Tran | |
| 2013/0110265 A1 | 5/2013 | Rahko et al. | |
| 2013/0130213 A1 | 5/2013 | Burbank et al. | |
| 2013/0155251 A1 | 6/2013 | Moravchik | |
| 2013/0178960 A1 | 7/2013 | Sheehan et al. | |
| 2013/0217541 A1 | 8/2013 | Shea | |
| 2013/0217542 A1 | 8/2013 | Shea | |
| 2013/0217543 A1 | 8/2013 | Shea | |
| 2013/0218309 A1 | 8/2013 | Napolitano | |
| 2013/0225369 A1 | 8/2013 | Fisbein et al. | |
| 2013/0304377 A1 | 11/2013 | Hende | |
| 2013/0325326 A1 | 12/2013 | Blumenberg et al. | |
| 2014/0000322 A1 | 1/2014 | Williams | |
| 2014/0124570 A1 | 5/2014 | Franklin | |
| 2014/0248996 A1 | 9/2014 | Adel | |
| 2014/0316701 A1 | 10/2014 | Cardonha et al. | |
| 2015/0081210 A1 | 3/2015 | Yeh et al. | |

FOREIGN PATENT DOCUMENTS

| | | | |
|---|---|---|---|
| JP | 2003131785 A | 5/2003 | |
| JP | 2005224318 | 8/2005 | |
| JP | 2007075172 | 3/2007 | |
| JP | 2008242063 | 10/2008 | |
| JP | 2009041964 A | 2/2009 | |
| JP | 2009142333 | 7/2009 | |
| JP | 2009194670 | 8/2009 | |
| JP | 2010088886 A | 4/2010 | |
| JP | 2012108801 A | 6/2012 | |
| JP | 2012189415 | 10/2012 | |
| JP | 2013050454 A | 3/2013 | |
| WO | 2009075493 A2 | 6/2009 | |
| WO | 2012070019 A2 | 5/2012 | |
| WO | 2012176193 A1 | 12/2012 | |
| WO | 2013055380 | 4/2013 | |

OTHER PUBLICATIONS

Veli-Jussi Raitila, "Tag, you're it—NFC in a home environment" TKK T-110.5190 Seminar on Internertworking, Finland, pp. 1-6, 2007. http://www.tml.tkk.fi/Publications/C/23/papers/Raitila_final.pdf.

PCT International Search Report and Written Opinion for related application PCT/US2014/055579 dated Dec. 22, 2014.

PCT International Search Report and Written Opinion for related application PCT/US2014/055585 dated Dec. 17, 2014.

Sabrina Tai-Chen Yeh, Takashi Hironaka, David Andrew Young, Steven Friedlander, "Quick Login to User Profile on Exercise Machine", related U.S. Appl. No. 14/037,263, Non-Final Office Action dated May 27, 2015.

Sabrina Tai-Chen Yen, Takashi Hironaka, David Andrew Young, Steven Friedlander, "Quick Login to User Profile on Exercise Machine", related U.S. Appl. No. 14/037,263, Applicant's response to Non-Final Office Action filed May 29, 2015.

Sabrina Tai-Chen Yeh, David Andrew Young, Takashi Hironaka, Steven Friedlander, "Nonverbal Audio Cues During Physical Activity", related U.S. Appl. No. 14/037,271, Non-Final Office Action dated Jul. 2, 2015.

Sabrina Tai-Chen Yeh, David Andrew Young, Takashi Hironaka, Steven Friedlander, "Nonverbal Audio Cues During Physical Activity", related U.S. Appl. No. 14/037,271, Applicant's response to Non-Final Office Action filed Jul. 13, 2015.

Julia Anne Framel, Aravind Babu Asam, Guru Prashanth Balasubramanian, Takeshi Suzuki, Charles D. Hedrick, "User Device Position Indication for Security and Distributed Race Challenges", related U.S. Appl. No. 14/261,075, Non-Final Office Action dated Mar. 23, 2015.

Sabrina Tai-Chen Yeh, David Andrew Young, Steven Friedlander, Determining Exercise Routes Based on Device Determined Information, related U.S. Appl. No. 14/037,276, Non-Final Office Action dated Mar. 31, 2015.

Sabrina Tai-Chen Yeh, David Andrew Young, Steven Friedlander, Determining Exercise Routes Based on Device Determined Information, related U.S. Appl. No. 14/037,276, Applicant's response to Non-Final Office Action filed Apr. 1, 2015.

Julia Anne Framel, Aravind Babu Asam, Guru Prashanth Balasubramamanian, "User Device Position Indication for Security and Distributed Race Challenges", related U.S. Appl. No. 14/261,075, Applicant's response to Non-Final Office Action filed Mar. 30, 2015.

Sabrina Tai-Chen Yeh, David Andrew Young, "Altering Exercise Routes Based on Device Determined Information", related U.S. Appl. No. 14/037,286, Non-Final Office Action dated Aug. 28, 2015.

Sabrina Tai-Chen Yeh, David Andrew Young, "Altering Exercise Routes Based on Device Determined Information", related U.S. Appl. No. 14/037,286, Applicant's response to Non-Final Office Action filed Sep. 8, 2015.

Sabrina Tai-Chen Yeh, Steven Friedlander, David Andrew Young, "Presenting Audio Based on Biometrics Parameters", related U.S. Appl. No. 14/037,252, Non-Final Office Action dated Aug. 4, 2015.

Sabrina Tai-Chen Yeh, Takashi Hironaka, David Andrew Young, Steven Friedlander, "Quick Login to User Profile on Exercise Machine", related U.S. Appl. No. 14/037,263, Final Office Action dated Aug. 20, 2015.

Sabrina Tai-Chen Yeh, Takashi Hironaka, David Andrew Young, Steven Friedlander, "Quick Login to User Profile on Exercise Machine", related U.S. Appl. No. 14/037,263, Applicant's response to Final Office Action filed Aug. 25, 2015.

Sabrina Tai-Chen Yeh, David Andrew Young, Steven Friedlander, "Determining Exercise Routes Based on Device Determined Information", related U.S. Appl. No. 14/037,276, Final Office Action dated Jun. 15, 2015.

Sabrina Tai-Chen Yeh, David Andrew Young, Steven Friedlander, "Determining Exercise Routes Based on Device Determined Information", related U.S. Appl. No. 14/037,276, Applicant's response to Final Office Action filed Jun. 17, 2015.

Jason Michael Warner, "Devices and Methods for Health Tracking and Providing Information for Improving Health", related U.S. Appl. No. 14/160,871, Non-Final Office Action dated Sep. 30, 2015.

Jason Michael Warner, "Devices and Methods for Health Tracking and Providing Information for Improving Health", related U.S. Appl. No. 14/160,871, Applicant's response to Non-Final Office Action filed Oct. 2, 2015.

Sabrina Tai-Chen Yeh, David Andrew Young, "Altering Exercise Routes Based on Device Determined Information", file history of related U.S. Appl. No. 14/037,286, filed Sep. 25, 2013.

Sabrina Tai-Chen Yeh, Steven Friedlander, David Andrew Young, "Nonverbal Audio Cues During Physical Activity", file history of related U.S. Appl. No. 14/037,278, filed Sep. 25, 2013.

Sabrina Tai-Chen Yeh, Takashi Hironaka, David Andrew Young, Steven Friedlander, "Quick Login to User Profile on Exercise Machine", file history of related U.S. Appl. No. 14/037,263, filed Sep. 25, 2013.

Sabrina Tai-Chen Yeh, David Andrew Young, Steven Friedlander, "Determine Exercise Routes Based on Device Determined Information", file history of related U.S. Appl. No. 14/037,276, filed Sep. 25, 2013.

Sabrina Tai-Chen Yeh, Steven Friedlander, David Andrew Young, "Synchronized Exercise Buddy Headphones", file history of related U.S. Appl. No. 14/037,267, filed Sep. 25, 2013.

Sabrina Tai-Chen Yeh, David Andrew Young, Takashi Hironaka, Steven Friedlander, "Presenting Audio Based on Biometrics Parameters", file history of related U.S. Appl. No. 14/037,271, filed Sep. 25, 2013.

Sabrina Tai-Chen Yeh, Steven Friedlander, David Andrew Young, "Presenting Audio Video on Biometrics Parameters", file history of related U.S. Appl. No. 14/037,252, filed Sep. 25, 2013.

Sabrina Tai-Chen Yeh, Jenny Therese Fredriksson, "Combining Data Sources to Provide Accurate Effort Monitoring", file history of related U.S. Appl. No. 14/037,224, filed Sep. 25, 2013.

Sabrina Tai-Chen Yeh, Jenny Therese Fredriksson, "Intelligent Device Mode Shifting Based on Activity", file history of related U.S. Appl. No. 14/037,228, filed Sep. 25, 2013.

(56) References Cited

OTHER PUBLICATIONS

Jason Michael Warner, "Devices and Methods for Health Tracking and Providing Information for Improving Health", file history of related U.S. Appl. No. 14/160,871, filed Jan. 22, 2014.

Julia Anne Framel, Aravind Babu Asam, Guru Prashanth Balasubramanian, Takeshi Suzuki, Charles D. Hedrick Jr., "User Device Position Indication for Security and Distributed Race Challenges", file history of related U.S. Appl. No. 13/644,044, filed Oct. 3, 2012.

* cited by examiner

COMBINING DATA SOURCES TO PROVIDE ACCURATE EFFORT MONITORING

This application claims priority to U.S. provisional patent application Ser. No. 61/878,835, filed Sep. 17, 2013.

FIELD OF THE INVENTION

The present application relates generally to digital ecosystems that are configured for use when engaging in physical activity and/or fitness exercises.

BACKGROUND OF THE INVENTION

Society is becoming increasingly health-conscious. A wide variety of exercise and workouts are now offered to encourage people to stay fit through exercise. As understood herein, while stationary exercise equipment often comes equipped with, data displays for the information of the exerciser, the information is not tailored to the individual and is frequently repetitive and monotonous. As further understood herein, people enjoy listening to music as workout aids but the music typically is whatever is broadcast within a gymnasium or provided on a recording device the user may wear, again being potentially monotonous and unchanging in pattern and beat in a way that is uncoupled from the actual exercise being engaged in. Furthermore, general fitness devices that monitor physical exertion during exercise do not always seem to provide an accurate enough picture of true effort.

SUMMARY OF THE INVENTION

Present principles recognize that by combining data from different sensors (on fitness device, mobile smartphone, smart clothing, other devices/people in same location/time), a monitoring system can provide a better indicator of true effort. This might not necessarily be a quantified "calories" or "distance", but a way to factor in 'difficulty' to help provide more nuance and qualification to a quantified measurement.

Accordingly, a device includes a computer readable storage medium bearing instructions executable by a processor, and a processor configured for accessing the computer readable storage medium to execute the instructions to configure the processor for receiving signals from a position sensor from which the processor can calculate a speed and a distance over an interval of time ΔT. The processor is configured for receiving a signal representing a weather condition, and another signal representing a biometric condition of a user of the device. The processor then adjusts a baseline value associated with the speed and/or distance based on the biometric condition and weather condition to render an adjusted baseline, and outputs an indicia of exercise effort based on the adjusted baseline.

In some embodiments, the processor when executing the instructions is further configured for receiving a signal representing a slope of terrain associated with the exercise effort, and adjusting the baseline value based on the slope. The processor also may receive a signal representing an elevation and/or type of terrain associated with the exercise effort, and adjust the baseline value based on the elevation and/or type.

The weather condition can include one or more of humidity, temperature, barometric pressure, and wind condition. The biometric condition can include one or more of heart rate, leg stride condition, sleep condition, and skin temperature.

In another aspect, a method includes establishing a baseline effort indicator at least partially based on a pace and distance of an exercise of a person. The baseline effort indicator is adjusted based on a biometric condition of the person, a weather condition, and a terrain condition, and an adjusted effort indicator is output based at least in part on the adjusting steps.

In another aspect, a device includes a computer readable storage medium bearing instructions executable by a processor, and a processor configured for accessing the computer readable storage medium to execute the instructions to configure the processor for combining data from at least one biometric sensor and one or more of weather information and terrain information. This provides an indication of an individual's physical effort during an exercise to enhance quantified metrics and provide an accurate picture of an individual's exercise and activity.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
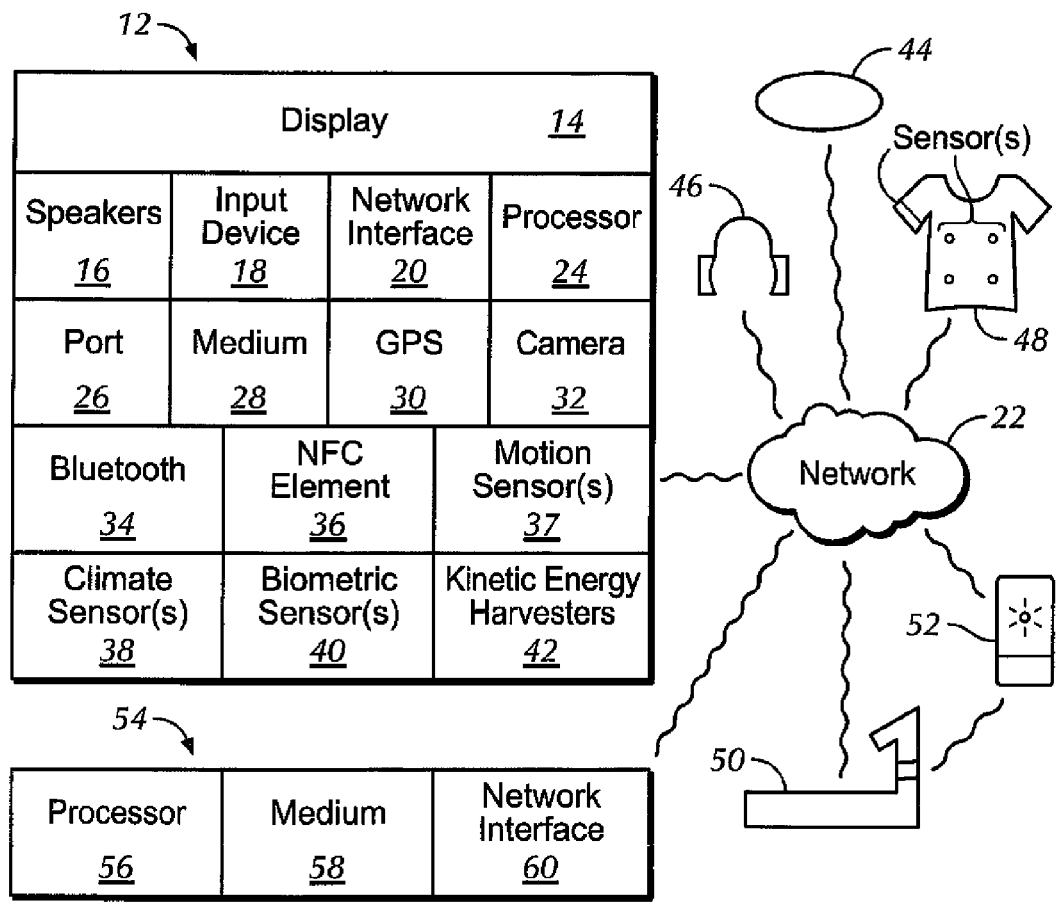
FIG. 1 is a block diagram of an example system including an example in accordance with present principles.

This disclosure relates generally to consumer electronics (CE) device based user information. A system herein may include server and client components, connected over a network such that data may be exchanged between the client and server components. The client components may include one or more computing devices including portable televisions (e.g. smart TVs, Internet-enabled TVs), portable computers such as laptops and tablet computers, and other mobile devices including smart phones and additional examples discussed below. These client devices may operate with a variety of operating environments. For example, some of the client computers may employ, as examples, operating systems from Microsoft, or a Unix operating system, or operating systems produced by Apple Computer or Google. These operating environments may be used to execute one or more browsing programs, such as a browser made by Microsoft or Google or Mozilla or other browser program that can access web applications hosted by the Internet servers discussed below.

Servers may include one or more processors executing instructions that configure the servers to receive and transmit data over a network such as the Internet. Or, a client and server can be connected over a local intranet or a virtual private network.

Information may be exchanged over a network between the clients and servers. To this end and for security, servers and/or clients can include firewalls, load balancers, temporary storages, and proxies, and other network infrastructure for reliability and security. One or more servers may form an apparatus that implement methods of providing a secure community such as an online social website to network members.

As used herein, instructions refer to computer-implemented steps for processing information in the system. Instructions can be implemented in software, firmware or hardware and include any type of programmed step undertaken by components of the system.

A processor may be any conventional general purpose single- or multi-chip processor that can execute logic by means of various lines such as address lines, data lines, and control lines and registers and shift registers.

Software modules described by way of the flow charts and user interfaces herein can include various sub-routines, procedures, etc. Without limiting the disclosure, logic stated to be executed by a particular module can be redistributed to other software modules and/or combined together in a single module and/or made available in a shareable library.

Present principles described herein can be implemented as hardware, software, firmware, or combinations thereof; hence, illustrative components, blocks, modules, circuits, and steps are set forth in terms of their functionality.

Further to what has been alluded to above, logical blocks, modules, and circuits described below can be implemented or performed with a general purpose processor, a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

The functions and methods described below, when implemented in software, can be written in an appropriate language such as but not limited to C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and digital subscriber line (DSL) and twisted pair wires. Such connections may include wireless communication connections including infrared and radio.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Before describing FIG. 1, it is to be understood that the CE devices and software described herein are understood to be usable in the context of a digital ecosystem. Thus, as understood herein, a computer ecosystem, or digital ecosystem, may be an adaptive and distributed socio-technical system that is characterized by its sustainability, self-organization, and scalability. Inspired by environmental ecosystems, which consist of biotic and abiotic components that interact through nutrient cycles and energy flows, complete computer ecosystems consist of hardware, software, and services that in some cases may be provided by one company, such as Sony Electronics. The goal of each computer ecosystem is to provide consumers with everything that may be desired, at least in part services and/or software that may be exchanged via the Internet. Moreover, interconnectedness and sharing among elements of an ecosystem, such as applications within a computing cloud, provides consumers with increased capability to organize and access data and presents itself as the future characteristic of efficient integrative ecosystems.

Two general types of computer ecosystems exist: vertical and horizontal computer ecosystems. In the vertical approach, virtually all aspects of the ecosystem are associated with the same company (e.g. produced by the same manufacturer), and are specifically designed to seamlessly interact with one another. Horizontal ecosystems, one the other hand, integrate aspects such as hardware and software that are created by differing entities into one unified ecosystem. The horizontal approach allows for greater variety of input from consumers and manufactures, increasing the capacity for novel innovations and adaptations to changing demands. But regardless, it is to be understood that some digital ecosystems, including those referenced herein, may embody characteristics of both the horizontal and vertical ecosystems described above.

Accordingly, it is to be further understood that these ecosystems may be used while engaged in physical activity to e.g. provide inspiration, goal fulfillment and/or achievement, automated coaching/training, health and exercise analysis, convenient access to data, group sharing (e.g. of fitness data), and increased accuracy of health monitoring, all while doing so in a stylish and entertaining manner. Further still, the devices disclosed herein are understood to be capable of making diagnostic determinations based on data from various sensors (such as those described below in reference to FIG. 1) for use while exercising, for exercise monitoring (e.g. in real time), and/or for sharing of data with friends (e.g. using a social networking service) even when not all people have the same types and combinations of sensors on their respective CE devices.

Thus, it is to be understood that the CE devices described herein may allow for easy and simplified user interaction with the device so as to not be unduly bothersome or encumbering e.g. before, during, and after an exercise.

Now specifically referring to FIG. 1, an example system 10 is shown, which may include one or more of the example devices mentioned above and described further below to enhance fitness experiences in accordance with present principles. The first of the example devices included in the system 10 is an example consumer electronics (CE) device 12 that may be waterproof (e.g., for use while swimming). The CE device 12 may be, e.g., a computerized Internet enabled ("smart") telephone, a tablet computer, a notebook computer, a wearable computerized device such as e.g. computerized Internet-enabled watch, a computerized Internet-enabled bracelet, other computerized Internet-enabled fitness devices, a computerized Internet-enabled music player, computerized Internet-enabled head phones, a computerized Internet-enabled implantable device such as an implantable skin device, etc., and even e.g. a computerized Internet-enabled television (TV). Regardless, it is to be understood that the CE device 12 is configured to undertake present principles (e.g. communicate with other CE devices to undertake present principles, execute the logic described herein, and perform any other functions and/or operations described herein).

Accordingly, to undertake such principles the CE device 12 can include some or all of the components shown in FIG. 1. For example, the CE device 12 can include one or more touch-enabled displays 14, one or more speakers 16 for outputting audio in accordance with present principles, and at least one additional input device 18 such as e.g. an audio receiver/microphone for e.g. entering audible commands to the CE device 12 to control the CE device 12. The example CE device 12 may also include one or more network interfaces 20 for communication over at least one network 22 such as the Internet, an WAN, an LAN, etc. under control of one or more processors 24. It is to be understood that the processor 24 controls the CE device 12 to undertake present principles, including the other elements of the CE device 12 described herein such as e.g. controlling the display 14 to present images thereon and receiving input therefrom. Furthermore, note the network interface 20 may be, e.g., a wired or wireless modem, or router, or other appropriate interface such as, e.g., a wireless telephony transceiver, WiFi transceiver, etc.

In addition to the foregoing, the CE device 12 may also include one or more input ports 26 such as, e.g., a USB port to physically connect (e.g. using a wired connection) to another CE device and/or a headphone port to connect headphones to the CE device 12 for presentation of audio from the CE device 12 to a user through the headphones. The CE device 12 may further include one or more tangible computer readable storage medium 28 such as disk-based or solid state storage, it being understood that the computer readable storage medium 28 may not be a carrier wave. Also in some embodiments, the CE device 12 can include a position or location receiver such as but not limited to a GPS receiver and/or altimeter 30 that is configured to e.g. receive geographic position information from at least one satellite and provide the information to the processor 24 and/or determine an altitude at which the CE device 12 is disposed in conjunction with the processor 24. However, it is to be understood that that another suitable position receiver other than a GPS receiver and/or altimeter may be used in accordance with present principles to e.g. determine the location of the CE device 12 in e.g. all three dimensions.

Continuing the description of the CE device 12, in some embodiments the CE device 12 may include one or more cameras 32 that may be, e.g., a thermal imaging camera, a digital camera such as a webcam, and/or a camera integrated into the CE device 12 and controllable by the processor 24 to gather pictures/images and/or video in accordance with present principles (e.g. to share aspects of a physical activity such as hiking with social networking friends). Also included on the CE device 12 may be a Bluetooth transceiver 34 and other Near Field Communication (NFC) element 36 for communication with other devices using Bluetooth and/or NFC technology, respectively. An example NFC element can be a radio frequency identification (RFID) element.

Further still, the CE device 12 may include one or more motion sensors 37 (e.g., an accelerometer, gyroscope, cyclometer, magnetic sensor, infrared (IR) motion sensors such as passive IR sensors, an optical sensor, a speed and/or cadence sensor, a gesture sensor (e.g. for sensing gesture command), etc.) providing input to the processor 24. The CE device 12 may include still other sensors such as e.g. one or more climate sensors 38 (e.g. barometers, humidity sensors, wind sensors, light sensors, temperature sensors, etc.) and/or one or more biometric sensors 40 (e.g. heart rate sensors and/or heart monitors, calorie counters, blood pressure sensors, perspiration sensors, odor and/or scent detectors, fingerprint sensors, facial recognition sensors, iris and/or retina detectors, DNA sensors, oxygen sensors (e.g. blood oxygen sensors and/or VO2 max sensors), glucose and/or blood sugar sensors, sleep sensors (e.g. a sleep tracker), pedometers and/or speed sensors, body temperature sensors, nutrient and metabolic rate sensors, voice sensors, lung input/output and other cardiovascular sensors, etc.) also providing input to the processor 24. In addition to the foregoing, it is noted that in some embodiments the CE device 12 may also include a kinetic energy harvester 42 to e.g. charge a battery (not shown) powering the CE device 12.

Still referring to FIG. 1, in addition to the CE device 12, the system 10 may include one or more other CE device types such as, but not limited to, a computerized Internet-enabled bracelet 44, computerized Internet-enabled headphones and/or ear buds 46, computerized Internet-enabled clothing 48, a computerized Internet-enabled exercise machine 50 (e.g. a treadmill, exercise bike, elliptical machine, etc.), etc. Also shown is a computerized Internet-enabled gymnasium entry kiosk 52 permitting authorized entry to a gymnasium housing the exercise machine 50. It is to be understood that other CE devices included in the system 10 including those described in this paragraph may respectively include some or all of the various components described above in reference to the CE device 12 such but not limited to e.g. the biometric sensors and motion sensors described above, as well as the position receivers, cameras, input devices, and speakers also described above.

Thus, for instance, the headphones/ear buds 46 may include a heart rate sensor configured to sense a person's heart rate when a person is wearing the head phones, the clothing 48 may include sensors such as perspiration sensors, climate sensors, and heart sensors for measuring the intensity of a person's workout, and the exercise machine 50 may include a camera mounted on a portion thereof for gathering facial images of a user so that the machine 50 may thereby determine whether a particular facial expression is indicative of a user struggling to keep the pace set by the exercise machine 50 and/or an NFC element to e.g. pair the machine 50 with the CE device 12 and hence access a database of preset workout routines, and the kiosk 52 may include an NFC element permitting entry to a person authenticated as being authorized for entry based on input received from a complimentary NFC element (such as e.g. the NFC element 36 on the device 12). Also note that all of the devices described in reference to FIG. 1, including a server 54 to be described shortly, may communicate with each other over the network 22 using a respective network interface included thereon, and may each also include a computer readable storage medium that may not be a carrier wave for storing logic and/or software code in accordance with present principles.

Now in reference to the afore-mentioned at least one server 54, it includes at least one processor 56, at least one tangible computer readable storage medium 58 that may not be a carrier wave such as disk-based or solid state storage, and at least one network interface 60 that, under control of the processor 56, allows for communication with the other CE devices of FIG. 1 over the network 22, and indeed may facilitate communication therebetween in accordance with present principles. Note that the network interface 60 may be, e.g., a wired or wireless modem or router, WiFi transceiver, or other appropriate interface such as, e.g., a wireless telephony transceiver.

Accordingly, in some embodiments the server 54 may be an Internet server, may facilitate fitness coordination and/or data exchange between CE device devices in accordance with present principles, and may include and perform "cloud" functions such that the CE devices of the system 10 may access a "cloud" environment via the server 54 in example embodiments to e.g. stream music to listen to while exercising and/or pair two or more devices (e.g. to "throw" music from one device to another).

Figure 2:
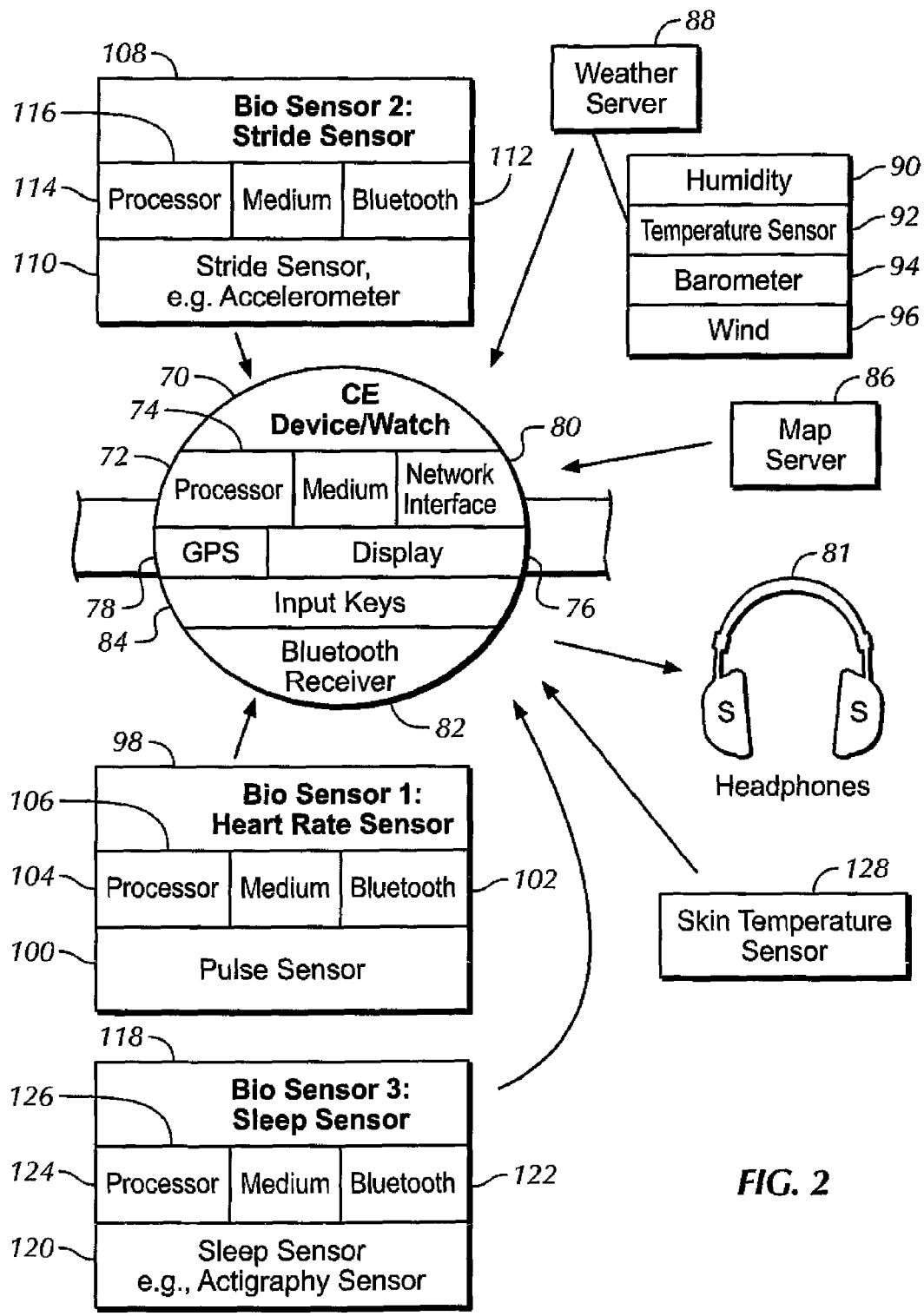
FIG. 2 is a block diagram of an example specific system.

FIG. 2 shows a more specific example of a system according to the general principles above. A CE device 70 may be embodied as a wristwatch as shown (or a mobile telephone or other portable CE device or combination of devices) and may include one or more microprocessors 72 accessing one or more computer readable storage media 74 to output visible information to the wearer on a display 76. Speakers also may be provided to output audible information. A position sensor such as a GPS sensor 78 may provide position information to the processor 72, from which the processor 72 can calculate a speed over an interval of time $\Delta T$ using the equation speed=distance/$\Delta T$.

The processor 72 also can receive information from Internet servers discussed further below using a wireless network interface 80 such as a WiFi or telephony interface. The processor 72 may communicate with nearby devices such as the biometric sensors discussed further below and such as audio headphones 81 using, for example, a Bluetooth transceiver 82 or a radiofrequency identification (REM) transceiver or other wireless and typically short range (<100 meters in useful transmission range) transceiver. User input of, e.g., recent food and beverage intake may be received on an input device 84 such as a keypad, microphone coupled to voice entry software, touch display, etc. The processor 72 may also access other information stored on the computer readable storage media 74 as received from another CE device or Internet server using one or more of the transceivers above. For example, the processor 72 may access calendar information of the user that lists future meetings and events for which the user is scheduled.

As discussed above, the processor 72 can receive information from various Internet servers or other network servers by means of the network interface 80. For example, the processor 72 can receive map information from a map server 86 from which, knowing its position from signals from the position sensor 78, the processor 72 can ascertain the elevation, slope, and other terrain information pertaining to the present location of the CE device 70.

Also, the processor 72 can receive local weather information from a weather server 88. The weather server 88 may access one or more of a humidity sensor 90, a temperature sensor 92, a barometer 94, and a wind sensor 96 and, in response to receiving a query from the processor 72 using the current location of the CE device 70 as derived from the position sensor 78 as an automatically uploaded entering argument, provide local weather conditions to the processor 72. The signals from the servers may be received by the CE device processor 72 through the appropriate communication interface and stored on the computer readable media 74 and/or on local cache memory associated with the processor 72, for processing of the information through the registers of the processor 72 according to description herein to provide output on the display 76 and/or headphones 81 or other output device.

In addition to accessing information from network servers, the processor 72 of the CE device 70 may access information from one or more biometric sensors that can be worn by or can otherwise be engaged with the user of the CE device 70. A heart rate sensor 98 may be provided as an example in which signals from a pulse sensor 100 are provided to the CE device 70 through a wireless transceiver 102 such as but not limited to a Bluetooth transceiver under control of one or more processors 104 accessing one or more computer readable media 106. The signals from the biometric sensor may be received by the CE device processor 72 through the appropriate communication interface and stored on the computer readable media 74 and/or on local cache memory associated with the processor 72, for processing of the information through the registers of the processor 72 according to description herein to provide output on the display 76 and/or headphones 81 or other output device.

A stride sensor 108 may be provided as another example in which signals from a stride sensor 110 (which may include, e.g., an accelerometer and/or gyroscope and/or force sensing resistor other jolt-sending or pressure-sensing device) are provided to the CE device 70 through a wireless transceiver 112 such as but not limited to a Bluetooth transceiver under control of one or more processors 114 accessing one or more computer readable media 116. The signals from the biometric sensor 108 may be received by the CE device processor 72 through the appropriate communication interface and stored on the computer readable media 74 and/or on local cache memory associated with the processor 72, for processing of the information through the registers of the processor 72 according to description herein to provide output on the display 76 and/or headphones 81 or other output device.

A sleep rate sensor 118 may be provided as another example (typically sensing sleep prior to exercise and data from which is stored by the CE device 70 for later retrieval according to principles discussed below) in which signals from a sleep quality sensor 120 (which may include an actigraphy-type mechanism) are provided to the CE device 70 through a wireless transceiver 122 such as but not limited to a Bluetooth transceiver under control of one or more processors 124 accessing one or more computer readable media 126. The signals from the biometric sensor 118 may be received by the CE device processor 72 through the appropriate communication interface and stored on the computer readable media 74 and/or on local cache memory associated with the processor 72, for processing of the information through the registers of the processor 72 according to description herein to provide output on the display 76 and/or headphones 81 or other output device.

Other biometric sensors may be provided, including a skin temperature sensor 128 that has onboard sensing, processing, and transceiving components similar to those discussed above in relation to other biometric sensors. The biometric sensors may be mounted on the CE device 70, fitness devices such as treadmills, mobile telephones, clothing worn by the user, or even other devices and/or people in the same location as the user at the same time as the user.

Figure 3:
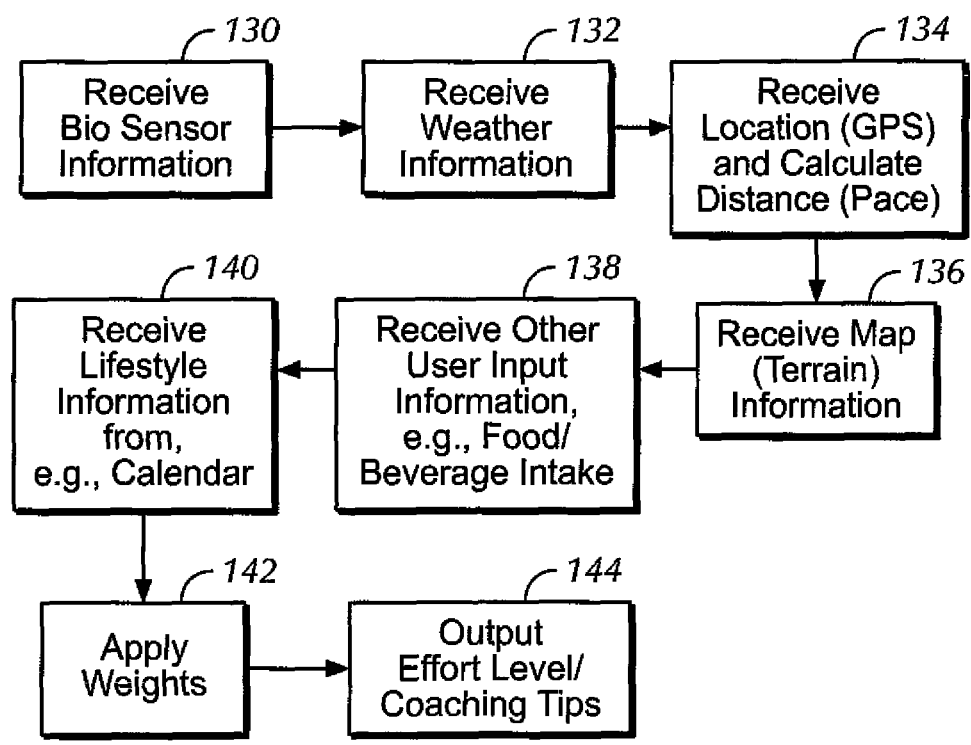
FIG. 3 is a flowchart of example logic.

FIG. 3 shows logic in which factors from multiple sources are combined to output an accurate effort monitoring output. As discussed further below, these factors can include personal biometrics such as instantaneous heart rate, skin temperature, pace (as derived from position signals per above description, e.g.,), stride length, and stride cadence. The factors also can include the duration of the exercise activity (as accessed from the internal processor clock of the CE device 70, for instance), location data such as position, absolute altitude, elevation gain (as derived from downloaded map data from the map server, for example), and terrain (type of surface for running as derived from downloaded map data). The factors may also include weather factors such as wind speed and direction, humidity, temperature, barometric pressure, and sun or cloud cover as derived from downloaded information from the weather server. Still further, the factors can include life context factors such as food intake as obtained from user input, stress levels as inferred from a number and frequency of meetings on the user's calendar data for example, and knowing the user's prior behavior as learned by the processor 72.

Accordingly, at block 130 in FIG. 3 the CE device 70 in FIG. 2 receives biometric information from one or more of the sensors shown in FIG. 2. Weather information from, e.g., the weather server 88 is received at block 132 and location information is received from the position sensor 78 at block 134. From this, the user's distance run and pace over an exercise period can be determined from the above.

Map and terrain information may be received at block 136 from, e.g., the map server 86, and user-input information can be received at block 138 by means of, e.g., the user input device 84 indicating food and beverage intake of the user for the past N hours. Lifestyle information as derived from, e.g., a number of upcoming or immediately past meetings within a threshold time period (for instance, within the past or future 24 hours) can be retrieved from calendar information or elsewhere at block 140.

Weights for each factor may be applied at block 142 if desired, with each factor having its own respective weight and with some factors optionally having the same weights as other factors, or with each factor having its own unique weight. The weights can be positive or negative, e.g., for a run up a slope the weight accorded to a slope factor may be positive while for a run down a slope the weight can be negative. An effort level and/or coaching tips are output at block 144 based on the weighted combined factors.

An example of the above now follows.

A baseline effort indicator may be established as a number between 0-100 based on the distance and pace (speed) of the workout. The longer the distance and the faster the pace, the higher the baseline number. Note that each baseline number for each user may be established for that user by averaging the first several workout times and distances and paces, so that a baseline for one user may not be the same as the baseline for another user.

That baseline number is then adjusted upwardly for factors that increase the difficulty of the workout and decreased downwardly for factors the decrease the difficulty of the workout. As examples:

For average workout heart rates in excess of a test value such as but not limited to a median rate or average rate or other test value, which can be empirically determined if desired, add A points (multiplied if desired by a heart rate weighting factor) to the baseline number, wherein A, like the other adjustment "points" referred to herein, can be an integer. For average workout heart rates below a median rate, subtract A points (multiplied if desired by a heart rate weighting factor) to the baseline number. The adjustment points "A", like the other adjustment points discussed below and designated by letters of the alphabet, can vary with the amount of excess/shortfall between the measured factor and the median. For example, the magnitude of "A" can increase (or decrease) linearly with the magnitude of the difference between the median and the measured value. Also, the median to which an excessive measurement value is compared may be the same as or different from the median to which a deficient measurement value is compared. Average values may be used, e.g., an average elevation or slope over the course of an exercise run or ride may be used. Or, instantaneous values may be used and the baseline adjusted and output updated accordingly.

For peak workout heart rates in excess of a median rate, which can be empirically determined if desired, add B points (multiplied if desired by a peak heart rate weighting factor) to the baseline number. For peak workout heart rates below a median rate, subtract B points (multiplied if desired by a peak heart rate weighting factor) to the baseline number.

For skin temperature in excess of a median, which can be empirically determined if desired, add C points (multiplied if desired by a skin temperature weighting factor) to the baseline number. For skin temperature below a median, which can be empirically determined if desired, subtract points (multiplied if desired by a skin temperature weighting factor) from the baseline number.

For stride length in excess of a median, which can be empirically determined if desired, add D points (multiplied if desired by a stride length weighting factor) to the baseline number. For stride length below a median, which can be empirically determined if desired, subtract points D (multiplied if desired by a stride length weighting factor) from the baseline number.

For stride cadence in excess of a median, which can be empirically determined if desired, add E points (multiplied if desired by a stride cadence weighting factor) to the baseline number. For stride cadence below a median, which can be empirically determined if desired, subtract E points (multiplied if desired by a stride length weighting factor) from the baseline number.

For sleep quality in excess of a median, which can be empirically determined if desired, subtract F points (multiplied if desired by a sleep quality weighting factor) from the baseline number. For sleep quality below a median, which can be empirically determined if desired, add F points (multiplied if desired by a sleep quality weighting factor) from the baseline number.

For ambient temperature in excess of a median, which can be empirically determined if desired, add G points (multiplied if desired by an ambient temperature weighting factor) to the baseline number. For ambient temperature below a median, which can be empirically determined if desired, subtract G points (multiplied if desired by an ambient temperature weighting factor) from the baseline number.

For ambient humidity in excess of a median, which can be empirically determined if desired, add H points (multiplied if desired by a humidity weighting factor) to the baseline number. For ambient humidity below a median, which can be empirically determined if desired, subtract H points (multiplied if desired by a humidity weighting factor) from the baseline number.

For ambient pressure in excess of a median, which can be empirically determined if desired, add I points (multiplied if desired by an ambient pressure weighting factor) to the baseline number. For ambient pressure below a median, which can be empirically determined if desired, subtract I points (multiplied if desired by an ambient pressure weighting factor) from the baseline number.

For the speed vector of the ambient wind that is directly against the user's direction of travel in excess of a median, which can be empirically determined if desired, add K points (multiplied if desired by an ambient wind weighting factor) to the baseline number. For a similar speed vector going with the user, subtract K points (multiplied if desired by an ambient wind weighting factor) from the baseline number.

For an upward slope of terrain in the direction of the user's travel in excess of a median, which can be empirically determined if desired, add L points (multiplied if desired by a slope weighting factor) to the baseline number. For a downward slope, subtract L points (multiplied if desired by a slope weighting factor) from the baseline number.

For a difficult terrain surface in excess of a median, which can be empirically determined if desired, add M points (multiplied if desired by a terrain weighting factor) to the baseline number. For an easy terrain, subtract M points (multiplied if desired by a terrain weighting factor) from the baseline number.

For a caloric intake within the last Z hours below a median which can be empirically determined if desired, add N points (multiplied if desired by a calorie weighting factor) to the baseline number. For a caloric intake within the last Z hours above a median which can be empirically determined if desired, subtract N points (multiplied if desired by a calorie weighting factor) from the baseline number.

For a number of meetings within the last Z hours below a median which can be empirically determined if desired, subtract P points (multiplied if desired by a stress weighting factor) from the baseline number. For a number of meetings within the last Z hours above a median which can be empirically determined if desired, add P points (multiplied if desired by a stress weighting factor) to the baseline number.

For a number of meetings in the next Z hours below a median which can be empirically determined if desired, subtract Q points (multiplied if desired by a stress weighting factor) from the baseline number. For a number of meetings in the next Z hours above a median which can be empirically determined if desired, add Q points (multiplied if desired by a stress weighting factor) to the baseline number.

For an elevation in excess of a median, which can be empirically determined if desired, add R points (multiplied if desired by an elevation weighting factor) to the baseline number. For elevation below a median, which can be empirically determined if desired, subtract R points (multiplied if desired by an elevation weighting factor) from the baseline number.

When all of the adjustments to the baseline number, such as some or all of the above, are made, an adjusted baseline number is arrived at. The magnitude of the adjusted baseline number may then be used to output an effort level and/or coaching tips. In one example, the magnitude of the adjusted baseline number may be used as entering argument in a table lookup as follows:

| Adjusted Baseline Number | Effort Level | Coaching Tip |
|---|---|---|
| 0-10 | very low | "need a lot more from you!" |
| 10-20 | moderately low | "try harder" |
| 20-30 | low | "try a little harder" |
| 30-40 | minimally low | "effort not quite there yet" |
| 40-50 | below average | "almost average" |
| 50-60 | above average | "doing OK today" |
| 60-70 | minimally high | "effort higher than expected" |
| 70-80 | high | "you are cranking it today!" |
| 80-90 | moderately high | "doing more than enough!" |
| 90-100 | very high | "take it easy Secretariat!" |

Figure 4:
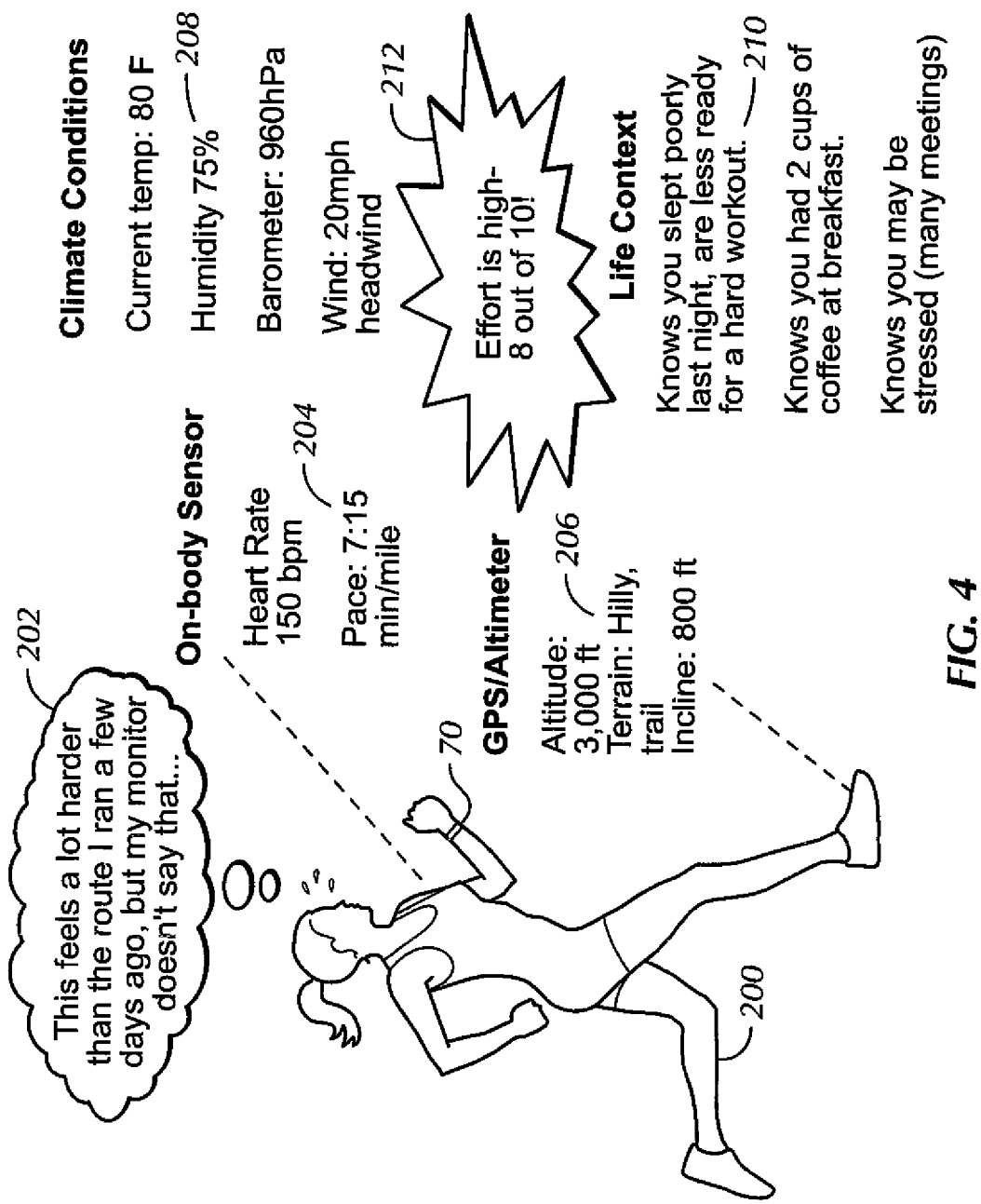
FIG. 4 is a schematic diagram illustrating present principles.

FIG. 4 shows that a runner 200 wearing the CE device 70 shown in FIG. 2 formerly would not have understood, as indicated by the thought balloon 202, why a workout felt harder than the CE device absent present principles indicated. However, when accounting according to present principles for biometric readings 204, terrain and position and slope 206, climate conditions 208, and life context conditions 210, an adjusted output 212 may be presented on the CE device 70 visibly and/or audibly correctly reflecting the combined factor effort level of the runner 200.

With no particular reference to any figure, it is to be understood that lactate sensors may also be included on, and/or in communication with, the CE devices described herein for sensing lactate levels, which can be e.g. measured in sweat, to thus determine an effort level in accordance with present principles and accordingly be another biometric parameter to be factored into a determination/adjustment of a baseline in accordance with present principles. Thus, e.g., for lactate levels in excess of a median, which can be empirically determined if desired, XYZ points may be added as set forth herein (multiplied if desired by a lactate level weighting factor) to the baseline number. For lactate levels below a median, which can be empirically determined if desired, points may be subtracted (multiplied if desired by a lactate level weighting factor) from the baseline number.

While the particular Combining Data Sources to Provide Accurate Effort Monitoring is herein shown and described in detail, it is to be understood that the subject matter which is encompassed by the present invention is limited only by the claims.

What is claimed is:

1. A device comprising:
   at least one computer readable storage medium bearing instructions executable by a processor;
   at least one processor configured for accessing the computer readable storage medium to execute the instructions to configure the processor for:
   receiving signals from a position sensor from which the processor can calculate a speed and a distance over an interval of time $\Delta T$;
   receiving at least one signal representing at least one biometric condition of a user of the device;
   adjusting a baseline value associated with the speed and/or distance based at least in part on the biometric condition to render an adjusted baseline; and
   outputting an indicia of exercise effort based at least in part on the adjusted baseline.

2. The device of claim 1 wherein the processor when executing the instructions is farther configured for:
   receiving at least one signal representing slope of terrain associated with the exercise effort; and
   adjusting the baseline value based at least in part on the slope.

3. The device of claim 1, wherein the processor when executing the instructions is further configured for:
   receiving at least one signal representing elevation of terrain associated with the exercise effort; and
   adjusting the baseline value based at least in part on the elevation.

4. The device of claim 1, wherein the processor when executing the instructions is further configured for:
   receiving at least one signal representing a type of terrain associated with the exercise effort; and
   adjusting the baseline value based at least in part on the type.

5. The device of claim 1, wherein the processor when executing the instructions is further configured for adjusting the baseline value based on humidity.

6. The device of claim 1, wherein the processor when executing the instructions is further configured for adjusting the baseline value based on temperature.

7. The device of claim 1, wherein the processor when executing the instructions is further configured for adjusting the baseline value based on barometric pressure.

8. The device of claim 1, wherein the processor when executing the instructions is further configured for adjusting the baseline value based on wind condition.

9. The device of claim 1, wherein the biometric condition includes heart rate.

10. The device of claim 1, wherein the biometric condition includes a leg stride condition.

11. A device comprising:
    at least one computer readable storage medium bearing instructions executable by a processor;
    at least one, processor configured for accessing the computer readable storage medium to execute the instructions to configure the processor for:
    receiving signals from a position sensor from which the processor cart calculate a speed and a distance over an interval of time $\Delta T$;
    receiving at least one signal representing at least one biometric condition of a user of the device;

adjusting a baseline value associated with the speed and/or distance based at least in part on the biometric condition to render an adjusted baseline; and outputting an indicia of exercise effort based at least in part on the adjusted baseline wherein the biometric condition includes a sleep condition.

12. The device of claim 1, wherein the biometric condition includes skin temperature.

13. Device comprising:

non-transitory computer readable storage medium (CRSM) bearing instructions executable by a processor which when executed by a processor configure the processor for:

establishing a baseline effort indicator at least partially based on a pace and distance of an exercise of a person;

adjusting the baseline effort indicator at least in part based on at least one biometric condition of the person;

adjusting the baseline effort indicator (BEI) at least in part based on at least one terrain condition; and outputting an adjusted effort indicator based at least in part on the adjusting steps.

14. The device of claim 13, wherein the instructions when executed by the processor configure the processor for, for average workout heart rates in excess of a test rate, increasing the BE and for average workout heart rates below a test rate, decreasing the BEI.

15. The device of claim 13, wherein the instructions when executed by the processor configure the processor for, for a terrain slope associated with the distance in excess of a test value, increasing the BEI and for terrain slope below a test value, decreasing BEI.

16. The device of claim 13, wherein the instructions when executed by the processor configure the processor for, for temperature in excess of a test value, increasing the BEI and for temperature below a test value, decreasing BEI.

17. The device of claim 13, wherein the instructions when executed by the processor configure the processor for, for humidity in excess of a test value, increasing the BEI and for humidity below a test value, decreasing BEI.

18. The device of claim 13, wherein the instructions when executed by the processor configure the processor for, for a wind value in excess of a test value, increasing the BEI and for a wind value below a test value, decreasing BEI.

19. The device of claim 13, wherein the instructions when executed by the processor configure the processor for, for a terrain elevation associated with the distance in excess of a test value, increasing the BEI and for terrain elevation below a test value, decreasing BEI.

20. A device, comprising:

at least one computer readable storage medium hearing instructions executable by a processor;

at least one processor configured for accessing the compute readable storage medium to execute the instructions to configure the processor for:

receiving terrain information;

combining data from at least one biometric sensor with the terrain information to render combined information; and providing an indication, based at least in part on the combined information, of an individual's physical effort during an exercise.

* * * * *